United States Patent
Love et al.

(10) Patent No.: US 6,328,763 B1
(45) Date of Patent: Dec. 11, 2001

(54) OPTIMIZED GEOMETRY OF A TISSUE PATTERN FOR SEMILUNAR HEART VALVE RECONSTRUCTION

(75) Inventors: Jack W. Love, Santa Barbara; James G. Hanlon, Camarillo, both of CA (US); Robert W. Suggitt, Vancouver (CA)

(73) Assignee: CardioMend, LLC, Santa Barbara, CA (US)

( * ) Notice: Subject to any disclaimer, the term of this patent is extended or adjusted under 35 U.S.C. 154(b) by 0 days.

(21) Appl. No.: 09/330,689

(22) Filed: Jun. 11, 1999

Related U.S. Application Data

(63) Continuation-in-part of application No. 08/626,342, filed on Apr. 2, 1996, which is a continuation-in-part of application No. 08/539,971, filed on Oct. 6, 1995, now Pat. No. 5,716,399.

(51) Int. Cl.[7] ........................................ A61F 2/24
(52) U.S. Cl. .................. 623/2.15; 623/2.13; 623/2.19; 623/2.42
(58) Field of Search ................... 623/2.12, 2.13, 623/2.15, 2.19, 2.42

(56) References Cited

U.S. PATENT DOCUMENTS

| | | | | |
|---|---|---|---|---|
| 2,292,003 | * | 8/1942 | Yant | 623/2.12 |
| 4,790,844 | * | 12/1988 | Ovil | 623/2.12 |
| 5,489,297 | * | 2/1996 | Duran | 623/2.12 |
| 5,628,792 | * | 5/1997 | Lentell | 623/2.12 |

* cited by examiner

*Primary Examiner*—Michael J. Milano
(74) *Attorney, Agent, or Firm*—Bryan Cave LLP

(57) ABSTRACT

A new and unique, optimized, two-dimensional heart valve tissue pattern, valve, and a method of reconstructing a three-dimensional semilunar heart valve, or portion thereof. In one preferred embodiment, the two-dimensional valve tissue pattern, and method of the present invention, comprises a two-dimensional configuration developed and optimized by employing, in part, the anatomy of a three-dimensional human heart valve, and said two-dimensional configuration delimits a two dimensional area that corresponds to the shape of tissue to be used in the repair of at least one leaflet of a circulatory system semilunar valve, wherein the configuration delimits at least one segment, and up to all three segments, of a three segment "trefoil" shape.

20 Claims, 3 Drawing Sheets

OPTIMIZED GEOMETRY OF A TISSUE PATTERN FOR SEMILUNAR HEART VALVE RECONSTRUCTION

CROSS-REFERENCE TO RELATED APPLICATIONS AND PATENTS

This application is a continuation-in-part of pending U.S. application Ser. No. 08/626,342 filed Apr. 2, 1996, which is a continuation-in-part of U.S. patent application Ser. No. 08/539,971, filed Oct. 6, 1995 (U.S. Pat. No. 5,716,399). U.S. application Ser. No. 08/626,342, and U.S. Pat. No. 5,716,399, are each incorporated herein, in their entirety, by this reference.

FIELD OF THE INVENTION

This invention relates generally to a new and improved heart valve tissue pattern and heart valve for semilunar heart valve reconstruction.

BACKGROUND OF THE INVENTION

For nearly forty years, since the advent of the heart-lung machine, it has been possible to reconstruct and replace heart valves.

The concept of repairing, rather than replacing, diseased heart valves began with the work of Professor Ake Senning of Zurich in 1960. (Senning A:Fascia lata replacement of aortic valves. *Journal of Thoracic Cardiovascular Surgery* 54:465–470 (1967)). Senning used autologous fascia lata to fashion three-dimensional aortic valve repairs with a free-hand technique, but subsequently abandoned his method by 1970 because of valve failures from thickening and shrinkage of the fresh, untreated tissue. Because of the experiences of Senning and others using similar techniques to repair or reconstruct heart valves with fresh autologous tissue, focus in the field of heart valve disease shifted from valve repair and reconstruction to full valve replacement with mechanical prostheses, and later, with bioprostheses made from heterograft (animal) tissue supported by a plastic or metal stent or frame.

Mechanical valves, such as the St. Jude Mechanical Bileaflet Valve, are often preferred because they have indefinite durability. Mechanical valves, however, also have inherent disadvantages, such as, for example, the danger of inducing blood clotting, thus requiring most patients to be on life-long anticoagulation medication. Mechanical valves also have less than ideal hemodynamic (blood flow) properties, they can be noisy, and the structural failures associated with such valves are usually catastrophic. Additional disadvantages are well known to those skilled in the art.

Heterograft (animal) tissue valves typically employ a semi-rigid frame, or stent, which supports animal tissue leaflets. Such stents are attached to the patient's heart with sutures. Tissue valves were originally believed to provide answers to most of the problems associated with mechanical valves: they significantly reduce the need for anticoagulation therapy, they have better, though not ideal, hemodynamic qualities, they are quiet, and their failure modes are generally slower, allowing time for surgical intervention to replace a failing valve. Clinical experience, however, has shown that such tissue valves have limited durability, for example, on the order of five to fifteen years. This limited durability is usually due to calcium build up on the foreign tissue, known as calcific degeneration, and is thought by several investigators to be caused by an immune response to the presence of a foreign tissue. There are also inherent disadvantages to using such frames, or stents, such as, for example, the space the stent occupies in the annular area thereby reducing effective valve orifice area, and possible abrasion of the tissue against the stent thereby causing or contributing to primary tissue failure of the valve.

Beginning in 1985, Love suggested using autologous pericardium, treated with a brief immersion in a glutaraldehyde solution, for use in an autologous tissue replacement for heart valves (Love et al. "Rapid intraoperative fabrication of an autogenous tissue heart valve: A new technique." *Proceedings of the Third International Symposium on Cardiac Bioprostheses* 691–698 (1986)). Later, Love reported that autologous pericardium, briefly treated in glutaraldehyde, does not thicken or shrink, is resistant to calcific degeneration, and is durable beyond 25 equivalent years in the accelerated life tester. (Love et al. Experimental evaluation of an autologous tissue heart valve. *Journal of Heart Valve Disease*, 1992; 1232–241). Others, such as Carpentier, a physician working on problems with the mitral valve, showed similar results (Chauvaud et al. "Valve extension with glutaraldehyde-preserved autologous pericardium" *Journal of Thoracic and Cardiovascular Surgery* 102:171–178 (1991)). Duran, another physician, resurrected Senning's techniques, and has used autologous pericardium treated with a brief immersion in glutaraldehyde for repair of diseased aortic valves, with good results, including lack of calcification. (Duran et al. "Indications and limitations of aortic valve reconstruction" *Annals of Thoracic Surgery* 52:447–454 (1991)).

In spite of the discovery that glutaraldehyde-treated autologous tissue, as opposed to fresh, untreated tissue, can be used as a material for heart valve replacement or repair, significant problems still exist with all of the reported approaches for repairing and reconstructing heart valves including, but not limited to, semilunar heart valves. These problems include, for example, that they are not standardized and they do not employ a relatively precise, pre-designed, reproducible, optimized pattern of two-dimensional tissue which, when attached to the aortic annulus and pressure loaded at physiologic levels, achieves normal or near normal three-dimensional anatomy when used to function as a semilunar heart valve.

In order to overcome the disadvantages of the prior art, as those skilled in the art will recognize and appreciate, there is an established need for an improved, more easily reproducible, less complicated, generally standardized, design and method of making a unitary valve tissue pattern to be used for the repair or reconstruction of a semilunar heart valve, having a generally simulated anatomical shape and good blood flow characteristics. The claimed invention provides a new, useful and unique two-dimensional valve tissue pattern design and method which may be used for easily fabricating three-dimensional heart valves for heart valve repair or reconstruction, which overcome many of the disadvantages of the prior art.

BRIEF SUMMARY OF THE INVENTION

The subject invention teaches a new and unique, optimized, two-dimensional heart valve tissue pattern, and a method of reconstructing a three-dimensional semilunar heart valve, or portion thereof, which pattern and valve are more efficient, more easily reproduced, less complicated to fabricate, and have enhanced performance characteristics.

In one preferred embodiment of the present invention, the improved two-dimensional valve tissue pattern of the present invention, prior to being affixed to a heart (and oriented into a three-dimensional valve, or a portion thereof), comprises a two-dimensional configuration that delimits a two dimensional area that corresponds to the shape of tissue to be used in the repair of at least one leaflet of a circulatory system semilunar valve, wherein the configuration delimits at least one segment, and up to all three segments, of a three segment "trefoil" shape. The anatomy of semilunar cardiac outflow valves typically have an essentially symmetrical tri-leaflet geometry with leaflet support provided by the scalloped annular attachment and the fixed length of the leaflet free edges extending from the commissures. The unique two-dimensional trefoil tissue pattern of the present invention can be made from any appropriate materials such as, for example, autologous tissue (including, for example, pericardium, facia lata and rectus sheath). Additional acceptable materials include heterograft (bovine, porcine, or other animal tissue) pericardium, synthetic materials, bioengineered materials, or any other like or suitable materials having appropriate plasticity and characteristics, as will be appreciated by those skilled in the art. In the preferred embodiment, autologous lightly tanned pericardium is used for the trefoil tissue pattern.

In one preferred embodiment, the valve tissue pattern is preferably created by cutting, shaping, or otherwise forming, essentially, a triangle, preferably equilateral in one embodiment, shaped orifice having linear or, in some alternative embodiments, non-linear sides such as, for example, concave sides, preferably in the center of a tissue pattern. The perimeter of the tissue pattern is preferably cut, shaped or otherwise formed into a pattern such that the perimeter of the pattern may be appropriately sutured or otherwise affixed to the annulus of the heart when the pattern is placed in an appropriate orientation. For convenience herein, the term annulus is used to denote the perimeter of the orifice opening where a heart valve is positioned. In a preferred embodiment, the two-dimensional perimeter of the trefoil valve tissue pattern, prior to being oriented to being affixed to the annulus of the heart, is preferably comprised of three, preferably rounded, outer edges with each respective outer edge corresponding to one leaflet attachment. When the two-dimensional trefoil valve tissue pattern, or a portion thereof, is oriented to be affixed to a heart, and after it is affixed to a heart, the perimeter of the tissue pattern of the present invention is preferably, essentially, a relatively circular or concentrically shaped pattern when viewed topographically. However, as will be appreciated by those skilled in the art, the shape of the annulus may effect the desired shape of the periphery of the two-dimensional trefoil valve tissue pattern and/or of the resulting valve, or portion thereof.

After the unique two-dimensional tissue pattern of the invention is cut, shaped or otherwise formed, the two-dimensional tissue pattern of one embodiment of the present invention may be preferably uniquely oriented and affixed to the annulus of a heart by, for example, suturing (using known or available suturing materials), stapling, or any other methods now or in the future known or used by those skilled in the art, without the use or need to affix any additional materials, such as a stent, to the valve tissue pattern or resulting valve, or portion thereof. The interior edges of the three respective portions of the trefoil valve pattern result in the creation of adequate coaptive area thereby facilitating for variations in the geometry of the resulting valve. The perimeter of the unique trefoil valve pattern is preferably affixed to the annulus of the heart, in one embodiment of the invention, by preferably first suturing (or otherwise affixing) the midpoint of each leaflet of the trefoil tissue pattern of the invention to the corresponding midpoint of each annular leaflet attachment. The suturing is preferably continued in distracted fashion toward the respective commissures. After the sutures are completed, the suture loops are preferably tightened by applying appropriate tension ensuring that each loop is properly aligned, thereafter the sutures are preferably tied or otherwise affixed at the commisures. Additional suture or affixation methods known or which may be known to those skilled in the art may be used including, for example, mattress sutures (bias stripped or non-bias stripped). Other methods for attachment including, for example, staples, can be used. As will be appreciated by those skilled in the art, in addition to the trefoil tissue pattern of the invention, as well as the unique valve of the invention, the invention also encompasses a tissue pattern comprising one or two valve leaflets for use in partial valve reconstructions. After the trefoil tissue pattern (or one or more leaflets thereof) of the present invention are affixed to the annulus of the heart, the tissue pattern will preferably deform under pressure into a valve, or portion thereof, having a geometry suitable for reconstruction of a diseased native valve, or portion thereof.

BRIEF DESCRIPTION OF THE DRAWINGS

FIG. 3(*b*) is a side view of a computer generated model of the normal human geometry of one leaflet of a closed valve;

FIG. 4(*b*) illustrates a preferred embodiment of the trefoil pattern of the invention;

Figure 1:
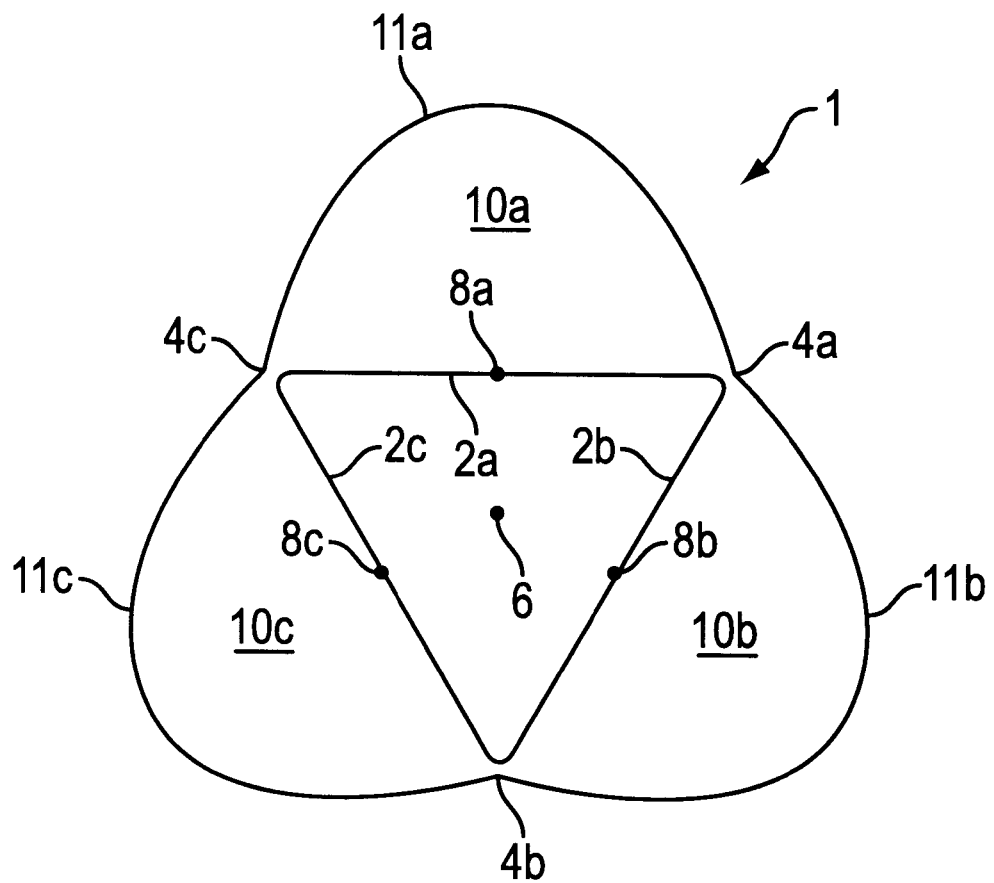
FIG. 1 illustrates a preferred embodiment of the trefoil tissue pattern of the invention.

The drawings are provided for illustrative purposes only and should not be used to unduly limit the scope of the invention.

DETAILED DESCRIPTION OF THE PREFERRED EMBODIMENTS

The subject invention is particularly suited for reconstruction of cardiac semilunar valves (aortic and pulmonic). The present invention teaches the design and development of a unique two-dimensional tissue pattern and the transformation of the two-dimensional tissue pattern into a three-dimensional valve reconstruction by attaching the tissue pattern in a proper orientation to the annulus and then loading the structure with the natural physiologic pressures and forces developed by the human heart and cardiovascular system.

The improved geometry of the preferred embodiment of the invention was developed in an effort to produce a reliable valve reconstruction which approximates the normal human aortic valve anatomy. The primary inventive and analytical steps employed to produce a preferred embodiment of the invention were to: (i) determine the mechanical characteristics and properties of a preferred material (autologous pericardium) to be used in a preferred embodiment employing engineering principles, apparatuses and procedures (including, for example, uniaxial tensile testing); (ii) assess how the preferred material having such characteristics and properties would behave when subjected to typical physiological loads and pressures; (iii) develop a unique two-dimensional tissue pattern employing the preferred material based upon (and by, in part, unwrapping) the normal geometry of a closed three-dimensional human semilunar heart valve; and (iv) employ finite element analysis modeling to assess the characteristics of the resulting two-dimensional valve tissue pattern.

In order to assess the geometry of a human aortic valve, and further optimize a unique two-dimensional human semilunar valve tissue pattern using information regarding normal human aortic valve geometry, a three-dimensional human aortic valve is preferably unwrapped employing the dimensional information and geometrical relationships reported by W. M. Swanson and R. E. Clark, "Dimensions and Geometric Relationships of the Human Aortic Value as a Function of Pressure," *Circulation Research*, Vol. 35, December 1974. Additional studies containing useful details regarding valve anatomy have been reported by others. See M. Thubrikar in, "The Aortic Valve," Boca Raton, Fla., *CRC Press*, 1990, p.9. Among the critical parameters identified by Swanson and Clark and by Thubrikar are the leaflet height, leaflet width at the commissural level, shape of the leaflet annular attachment, length of leaflet free edge, coaptive area during valve closure at a specified pressure, the angle of declination of the free edge when the valve is closed, and the resulting position of the point of central coaption. Swanson and Clark were the first to suggest that the loaded leaflet is a cylindrical section, rather than a spheroidal section. This was deduced from the straight line of the leaflet belly during loading as seen in profile view. Thubrikar accepted this interpretation on the basis of his own silicone molds. Additionally, Swanson and Clark express the dimensions of the valve leaflets as ratios of any particular dimension divided by the diameter of the annulus. For example, the leaflet length is expressed as the ratio of the leaflet length divided by the annulus diameter. For the free edge of the leaflet Swanson and Clark express an average ratio of 1.24.

Figure 2:
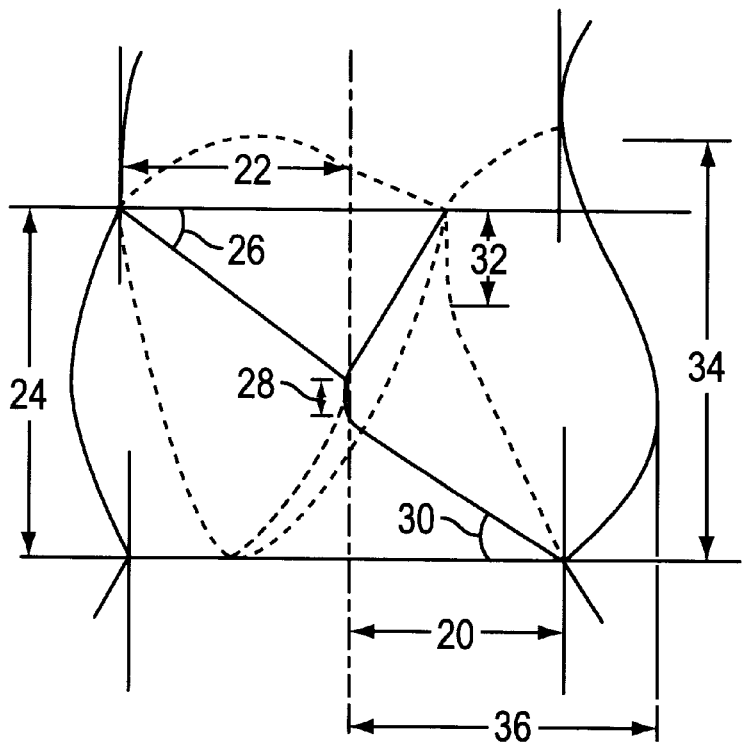
FIG. 2 is a prior art illustration of the human aortic valve.

FIG. 2 is a drawing reflecting the critical parameters and information reported by Thubrikar relating to the leaflets and sinus of a human semilunar valve which parameters include, as shown in FIG. 2, the radius 20 of the base, the radius 22 of the commissures, the height 24 of the valve, the angle of declination 26 of the free edge, the height 28 of central coaptive line, the bottom surface angle 30 of the leaflet, the height 32 of the commissure, the sinus height 34, and the radius 36 of the outermost sinus wall. (From M. Thubrikar: The Aortic Valve. Boca Raton, Fla., CRC Press, 1990, p 9.).

Figures 3A, 3B:
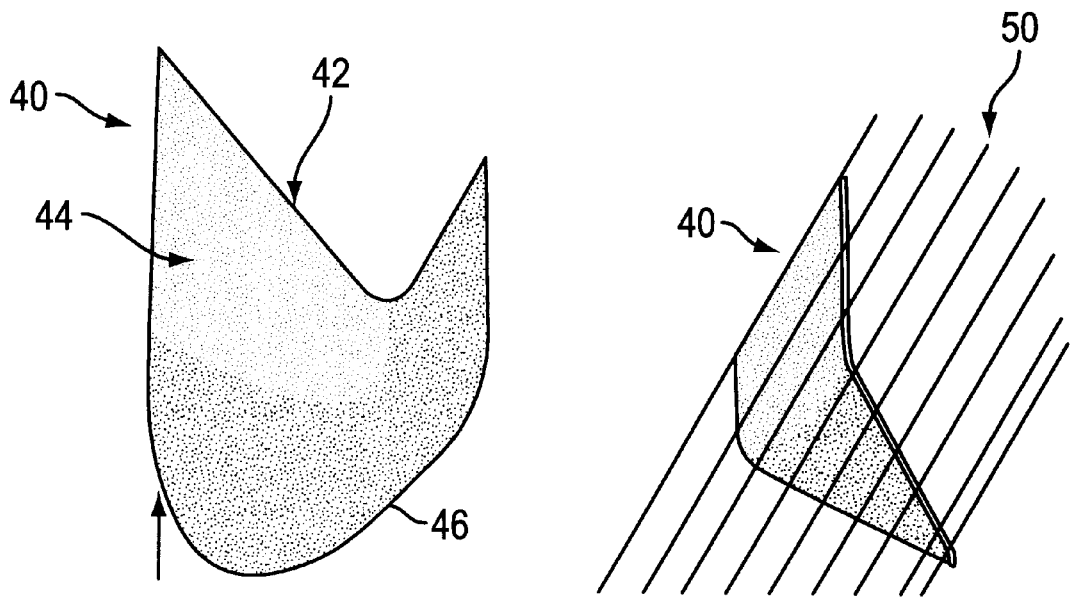
FIG. 3(*a*) is a computer generated model of the normal human geometry of one leaflet of a closed valve.

FIG. 3(*a*) is a computer generated drawing of the normal geometry of the native anatomy of a closed leaflet 40 having a representative 25 mm diameter of a semilunar human heart valve under 100 mmHg physiologic pressure. FIG. 3(*a*) shows the free edge 42, the coaptive surface 44, the belly 46, and the attachment line 48 of the closed leaflet 40. Using the computer generated drawing of the anatomically correct closed three-dimensional leaflet 40, as shown in FIG. 3(*b*), planar sections 50 were taken at 2.0 mm intervals through the closed leaflet 40, parallel to the free edge 42 of the closed leaflet 40. Leaflet widths along the line of intersection with the offset planes were measured. These widths were used with the leaflet central height to create an unwrapped, 2-dimensional leaflet shape, and by repetition at 120° arcs, to develop a unique, optimized, two-dimensional trefoil tissue pattern.

The finite element model employed to confirm and derive, in part, the geometry of the resulting two-dimensional trefoil tissue pattern 1 consisted of five principal steps. First, a flat semicircle is preferably created to represent one of the three leaflets 10*a*, 10*b* or 10*c*. Subsequently, the flat semicircle shape is preferably bent upwards into a cylindrical form so that the straight edge of the original shape (representing the leaflet free edge 2*a*, 2*b* or 2*c*) is preferably a semicircle. Next, the leaflet is preferably stretched into its fixed attachment line on the aortic wall. The next step is to preferably represent coaptation with the two neighboring leaflets, and a rigid, friction-free V-shaped surface is brought into contact with the leaflet. The apex of the V is preferably collinear with the axis of the aorta. This contact between the flexible leaflet and the rigid V-shaped surface creates the preferably friction free coaptive leaflet surfaces of the configured valve. Finally, a pressure of 20 kPa is preferably applied to the interior of the coapted leaflet to simulate typical physiological loading conditions. Due to its thinness, the leaflet of the present invention is preferably modeled using elastic shell elements. In order to account accurately for the stiffening of the pericardium and for the large shape changes that take place in vivo, large deformation elastic behavior may be used. Time stepping in the solution may be preferably adjusted to account for the geometric nonlinearities that occur with the large deformations. Additionally, parameters of the material properties may be generated by experimental stress-strain values from uniaxial testing of material (pericardium) strips.

A preferred embodiment of the two-dimensional trefoil valve tissue pattern 1 for valve leaflet repair is shown in FIG. 1. As shown in FIG. 1, the preferred embodiment of the two-dimensional tissue pattern 1 of the present invention is preferably, essentially, symmetrical around a central point 6. However, as those skilled in the art will appreciate, the lack of symmetry and shape of the annulus may effect the desired shape of the periphery of the two-dimensional trefoil valve tissue pattern and/or of the resulting valve, or portion thereof. Accordingly, the present invention may be asymmetrical and, thus, precise symmetry is not required. Central point 6 is preferably bordered by a triangular shaped orifice having relatively linear edges 2*a*, 2*b* and 2*c*, as shown in FIG. 1. In some alternative embodiments, edges 2*a*, 2*b* and 2*c* may be non-linear such as, for example, concave. Edges 2*a*, 2*b* and 2*c* define part of the coaption area of the closed valve when the two-dimensional trefoil tissue pattern is properly oriented into the three-dimensional valve of the invention and subject to physiological loads and pressures. The length of the edges 2*a*, 2*b* and 2*c* preferably define, approximately, the resulting diameter of the final valve reconstruction, although, in some instances, the length of edges 2*a*, 2*b* and 2*c*, may be slightly larger than the diameter of the final valve. It is known in the art that there is a range of symmetry for semilunar valves. See, e.g., Sands, et al., *Ann. Thorac. Surg.*, 8(5):407–14 (November 1969). The subject invention is applicable to the full range of anatomical valve sizes.

As shown in FIG. 1, a preferred embodiment of the two-dimensional trefoil valve tissue pattern 1 consists of three lobes, 10*a*, 10*b* and 10*c*. The outer peripheries of the three lobes 10*a*, 10*b* and 10*c* are preferably defined respectively by outer perimeter curves 11*a*, 11*b* and 11*c*. As shown in FIG. 1, outer perimeter curves 11*a*, 11*b* and 11*c* are preferably identical in shape (although, this is not a required characteristic of the invention) and said outer perimeter curves 11*a*, 11*b* and 11*c* have a variable radius, almost parabolic in shape, said radius being measured from corresponding mid-points 8*a*, 8*b* and 8*c* of edges 2*a*, 2*b* and 2*c*, respectively, of the equilateral triangle.

Each of lobes 10*a*, 10*b* and 10*c* of the two-dimensional trefoil valve tissue pattern of the present invention, when affixed to an annulus, oriented in a three-dimensional shape, and deformed under pressure, will form one leaflet or lobe of the valve structure. In one embodiment of the present invention, all three leaflets of a trileaflet valve are reconstructed with the trefoil valve tissue pattern. Alternatively, in other preferred embodiments of the present invention, only a portion of the trefoil pattern, one or two lobes, are employed to prepare tissue to reconstruct or repair one or more native leaflets of a valve. If a complete trefoil valve tissue pattern is used to reconstruct a valve, the three leaflets of the valve will preferably meet at a central coaption point.

The physical profile of the valve of the present invention is a characteristic defined in part by the length of the lobes. The lobe length 60, as the name suggests, is preferably the length of an individual leaflet in the two-dimensional trefoil valve tissue pattern. As will be appreciated by those skilled in the art, the longer the lobe length 60, the higher the profile of the resulting tri-leaflet valve structure of the invention, while, conversely, the shorter the lobe length 60, the shorter the profile of the resulting tri-leaflet valve structure.

As will be appreciated by those skilled in the art, the characteristics, dimensions, geometry, symmetry, and lack of symmetry, of the two-dimensional trefoil valve tissue pattern, and valve described herein will vary depending upon numerous variables and factors including, for example: the size and shape of the lobes 10*a*, 10*b* and 10*c*; the shape of the outer perimeter curves 11*a*, 11*b* and 11*c*; the geometry of (linear, non-linear, convex, or variations thereof) edges 2*a*, 2*b*, and 2*c*; the size, shape, dimensions and characteristics of the annulus, heart and circulatory system of the patient requiring valve reconstruction; and the mechanical properties of the tissue.

The unique two-dimensional trefoil tissue pattern of the present invention can be made from any appropriate materials such as, for example, autologous tissue including, for example, pericardium, fascia lata, rectus sheath (the fibrous tissue enveloping the abdominal muscles). Additional acceptable materials include heterograft (bovine, porcine, or other animal tissue) pericardium, synthetic materials, bioengineered materials, or any other like or suitable materials having appropriate plasticity and characteristics, as will be appreciated by those skilled in the art. Presently, the preferred tissue is autologous lightly tanned pericardium because of its: similarity to natural heart valve tissue; ability to undergo large deformations; strength; thickness; elastin content; collagen content; tensile strength; isotropic qualities; behavioral characteristics when put under load in the present invention; proven ability to serve as valve tissue for prolonged durations; enhanced ability to, preferably, avoid rejection and infection; and proximity to the heart and site of valve reconstruction (the tissue may be tested during a surgical procedure for conformity to necessary properties and then used for valve reconstruction during surgery). The success of a reconstruction depends in large part upon the biomechanical and physical properties of the tissue to ensure that the tissue has the necessary strength and deformation properties of the leaflets during normal cardiac cycling. For example, the radial and circumferential strength of the tissue preferably needs to be as uniform as possible (isotropic) to ensure equivalent action of each leaflet of the valve. Presently, it is believed that acceptable autologous pericardium should preferably be between 0.3 and 0.9 mm in thickness. Accordingly, in order to assess the properties of the proposed tissue, such tissue should preferably first undergo appropriate testing in order to ensure that the material meets or exceeds the appropriate tissue properties.

The tissue is preferably treated in order to stiffen it, and/or prevent tissue thickening and shrinkage. A preferred form of tissue treatment comprises use of glutaraldehyde to condition the tissue. For example, it has been found that immersion for about 10 minutes in a dilute glutaraldehyde solution, such as a 0.625% glutaraldehyde solution buffered to a pH of 7.4, produces acceptable results. As will be appreciated by those skilled in the art, there may now or in the future be additional methods to treat the tissue.

Autologous and heterograft pericardium appear to exhibit non-linear material elasticity and are readily stretched up to approximately fifteen percent (15%), after which point the tensile stiffness (modulus of elasticity) of the material increases by approximately two (2) orders of magnitude. This material behavior is beneficial to the use of the invention in that it permits the two-dimensional valve tissue material, when oriented into a three-dimensional valve shape and exposed to the loads and pressures in the cardiovascular system, to conform into a competent valve of the invention. These characteristics and properties are also favorable in that the materials ability to undergo large deformations and cyclical stresses, as is normally experienced in normal cardiac valve and valve leaflet action, will enhance the effectiveness, efficiency and life of the valve reconstruction.

Accordingly, because of these material properties, including, but not limited to, the non-linear elasticity of the materials, the presently preferred embodiment of the two-dimensional trefoil valve tissue pattern 1, made from autologous or heterograft pericardium, is uniformly scaled down (reduced in size) such that edges 2(*a*), 2(*b*) and 2(*c*) are ninety percent (90%) of the length that would normally be prepared to reconstruct a valve having a native anatomical size. As a result of the material's elastic properties, when the two-dimensional valve tissue pattern scaled down as described is oriented into a three-dimensional valve shape, affixed to the annulus, and exposed to the loads and pressures in the cardiovascular system, the pattern, or portion thereof, conforms to the anatomy of the normal, native valve and results in a competent valve. The optimal scalar reduction may be greater or less than ninety percent (90%).

Figures 4A, 4B:
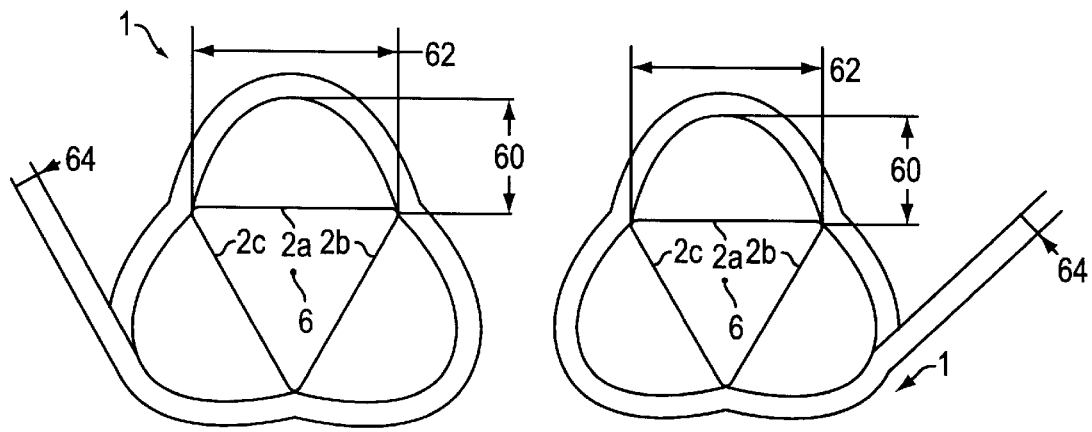
FIG. 4(*a*) illustrates a preferred embodiment of the trefoil pattern of the invention.

FIG. 4(*a*) reflects the preferred geometry, before the additional optimization of scaling down of the preferred embodiment of the invention. Based upon the work of Swanson and Clark, the average ratio of the lobe length 60 to the annulus is preferably 0.71. Before scaling down, as shown in FIG. 4(*a*), the lobe length 60 for a valve having a 25 mm annulus diameter under 100 mmHg pressure, based upon the two dimensional trefoil pattern of the present invention, would preferably be approximately 17.9 mm, and the length 62 of the free edges 2(*a*), 2(*b*) and 2(*c*) would preferably be approximately 29.6 mm. FIG. 4(*b*) exhibits the results of further optimizing the preferred embodiment of the invention shown in FIG. 4(*a*) by scaling the two-dimensional trefoil valve tissue pattern 1 down based upon, preferably, a ten percent (10%) (approximate) reduction in size of, for example, the preferable length 62 of the free edges (2(*a*), 2(*b*) and 2(*c*)) (26.3 mm, approximately) and the preferable length 60 of the lobes 10*a*, 10*b* and 10*c* (17.1 mm, approximately). As will be appreciated by those skilled in the art, the dimensions of the preferred embodiment may vary depending upon further research, refinement, developments, and the geometry required for a particular patient.

In a preferred embodiment, as shown in FIGS. 4(*a*) and 4(*b*), because the optimized trefoil tissue pattern must be affixed to an annulus, it is desireable to have a small amount of additional tissue on the margin of the perimeter of the valve tissue pattern to facilitate such affixation. Accordingly, in one preferred embodiment of the invention, a 3 mm margin of tissue 64 is added to the perimeter of the optimized two-dimensional valve tissue pattern.

In addition to the foregoing advantages, and those which will be obvious to those skilled in the art, the invention results in a reliably functioning valve having many additional features of a normal valve including, for example, a vertical coaptive surface and a depressed central coaptive line developed and increased along with an increase in the coaptive surface with increasing pressure. With the use of the novel trefoil valve tissue pattern, the coaptive surfaces increase in size with increased pressure, resulting in increased stability (if there is no leaflet prolapse). This method and invention is believed to produce a unique valve reconstruction having greater linear free edge lengths without the negative results caused by crimping or pinwheeling. As will be appreciated by those skilled in the art, although the two-dimensional valve tissue pattern shown in FIG. 1, and FIGS. 4(a) and 4(b) reflect the presently preferred pattern of the invention, further testing, both in vitro and in vivo, may result in additional refinements including, for example, the dimensions and geometry of the outer perimeter curves 11a, 11b and 11c may be modified, the optimal scalar reduction in size of the pattern may vary ±90%, and it may be desirable add some degree of convexity to edges 2(a), 2(b) and 2(c).

The geometry of the annulus to which the tissue pattern of the present invention is to be affixed in part establishes the geometry of the completed valve repair, obviating the need for a stent. Employment of the native annulus, which can include a remnant of native valve tissue, is another advantage of the present invention. The two-dimensional trefoil tissue pattern of one embodiment of the present invention may be preferably uniquely oriented and affixed to the annulus of a heart by, for example, suturing, without the addition or use of any further materials. The perimeter of the trefoil valve pattern is preferably affixed to the annulus of the heart, in one embodiment of the invention, by preferably first suturing the midpoint of each leaflet of the trefoil tissue pattern of the present invention to the corresponding midpoint of each annular leaflet attachment using a monofilament material. The suturing is preferably continued in distracted fashion toward the respective commissures. After the sutures are completed, the suture loops are preferably tightened by applying gentle tension ensuring that each loop is properly aligned, thereafter the sutures are preferably tied at the commisures. Additional suture methods may be used including, for example, interrupted distracted sutures, either bias striped or non-bias striped. Other means of fixation can be used, such as staples.

Figure 5:
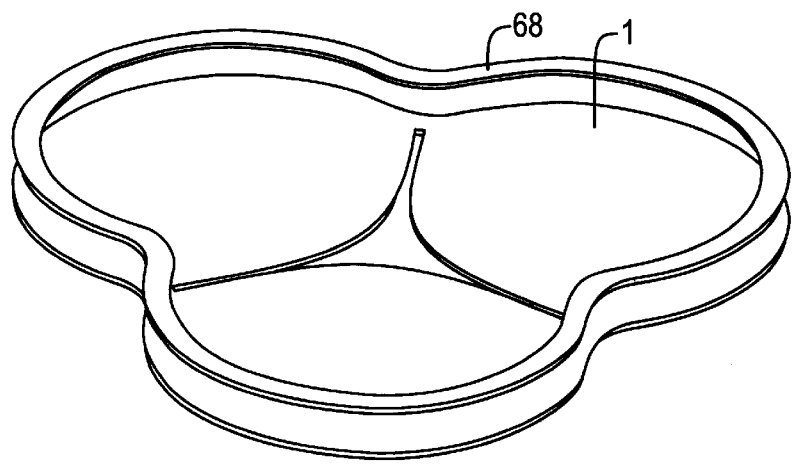
FIG. 5 illustrates a bias strip for reinforcing the outer margin of the trefoil valve tissue pattern of the invention.

An additional method of affixing the valve tissue pattern to the annulus involves the use of a bias strip 68 for reinforcing the outer margin of tissue at the base of the trefoil valve tissue pattern 1 which is sutured into the exposed annulus as shown in FIG. 5. As shown in FIG. 5, the bias strip 68 follows the same general outline as the trefoil valve tissue pattern. If a portion of trefoil valve tissue pattern 1 is used for valve repair, advantageously, the bias strip 68 is preferably constructed of a flexible biocompatible material such as thermoplastic or silicon, or a stiffened fabric such as "TEFLON" felt, "DACRON" felt, or "DACRON" velour. Advantageously, the bias strip 68 is at least partially situated over the edge portion extending around the outer periphery of the base of the trefoil valve tissue structure 1.

As will be appreciated by those skilled in the art, in addition to the trefoil tissue pattern of the present invention, and the unique valve of the present invention, the present invention also encompasses a tissue pattern comprising one or two valve leaflets, as well as partial valves for reconstruction of one or two valves.

Variations and modifications of the present invention will be apparent to those skilled in the art and the claims are intended to cover any variations and modifications falling within the true spirit and scope of the invention.

We claim:

1. A two-dimensional valve tissue pattern comprising a configuration that corresponds to the shape of tissue to be used in a reconstruction of at least one leaflet of a circulatory system valve, wherein the pattern comprises a configuration having three lobes arranged about a central coaption point within a central aperture.

2. The valve tissue pattern of claim 1 wherein each lobe is comprised of an outer perimeter and an inner edge.

3. The valve tissue pattern of claim 2 wherein the outer perimeter of each lobe has a rounded surface.

4. The valve tissue pattern of claim 3 wherein the inner edge of each lobe is linear.

5. The valve tissue pattern of claim 1 wherein said aperture has three sides.

6. The valve tissue pattern of claim 5 wherein the three lobes are asymmetrically arranged about the central coaption point.

7. The valve tissue pattern of claim 5 wherein the central aperture is a triangle.

8. The valve tissue pattern of claim 5 wherein the central aperature corresponds to the shape of an equilateral triangle in which each of the edges of said equilateral triangle correspond to a line of coaption on each of the lobes.

9. The valve tissue pattern of claim 8 wherein each lobe comprises an outer perimeter and an inner edge.

10. The valve tissue pattern of claim 9 wherein the outer perimeter of each lobe has a rounded surface.

11. The valve tissue pattern of claim 10 wherein each lobe meets adjacent lobes at commisure areas located at the point where the outer perimeter of each lobe meets the inner edge of the same lobe.

12. The valve tissue pattern of claim 1 wherein when the two-dimensional valve tissue pattern is affixed to the annulus of a heart, said valve tissue pattern forms to provide a competent valve leaflet reconstruction.

13. The valve tissue pattern of claim 5 wherein the three lobes are arranged in substantial radial symmetry about the central coaption point.

14. The valve tissue pattern of claim 9 wherein when the valve tissue pattern is affixed to the annulus of a heart, and said valve pattern forms a three-dimensional valve, the line of coaption of each lobe meets with the lines of coaption of the other two lobes.

15. The valve tissue pattern of claim 9 wherein the three lobes meet at a central coaption point.

16. The valve tissue pattern of claim 1 wherein the pattern is comprised of autologous, homologous or heterologous tissue.

17. The valve tissue pattern of claim 16 wherein said tissue is pericardium.

18. The valve tissue pattern of claim 1 wherein the two-dimensional tissue pattern is derived from unwrapping the three-dimensional geometry of a native anatomical circulatory system valve.

19. A two-dimensional valve tissue pattern comprising a configuration that corresponds to the shape of tissue to be used in the reconstruction of at least one leaflet of a native circulatory system valve, wherein the two-dimensional tissue pattern is reduced to a size which is smaller than the expected size of valve leaflets of a normal valve having a valve annulus of the size of the native circulatory system valve, such that when the tissue pattern is exposed to loads and pressures of the circulatory system, the tissue stretches and substantially conforms to the expected size of a normal valve.

20. The valve tissue pattern of claim 19 wherein the two-dimensional tissue pattern is reduced to a size which is approximately ten percent smaller than would normally be prepared to reconstruct a valve having a native anatomical size.

* * * * *